United States Patent [19]
Fullam

[11] Patent Number: 5,911,955
[45] Date of Patent: Jun. 15, 1999

[54] AROMA OIL CANDLE DIFFUSER RING

[75] Inventor: Philip S. Fullam, Chimayo, N.Mex.

[73] Assignee: New Venture Engineering, Inc., Santa Fe, N.Mex.

[21] Appl. No.: 08/824,448

[22] Filed: Mar. 26, 1997

[51] Int. Cl.⁶ .................................................... A61L 9/03
[52] U.S. Cl. ........................................... 422/125; 422/305
[58] Field of Search ................................ 422/5, 125, 305, 422/306; 431/289, 297

[56] References Cited

U.S. PATENT DOCUMENTS

| | | | |
|---|---|---|---|
| 729,019 | 5/1903 | Valentine | 422/125 |
| 989,019 | 4/1911 | Livingstone | 422/305 |
| 1,547,160 | 7/1925 | Bailey | 422/125 X |
| 1,966,738 | 7/1934 | Seewagen | 422/125 |
| 2,254,906 | 9/1941 | Petrulis | 422/125 |
| 2,435,756 | 2/1948 | Schlesinger | 422/125 X |
| 3,355,913 | 12/1967 | Frangos | 422/125 |
| 3,959,642 | 5/1976 | Turro | 422/125 X |
| 4,579,717 | 4/1986 | Gyulay | 422/125 |
| 4,647,428 | 3/1987 | Gyulay | 422/125 X |
| 4,781,895 | 11/1988 | Spector | 422/125 |
| 4,892,711 | 1/1990 | Tendick, Sr. | 422/125 |

FOREIGN PATENT DOCUMENTS 2294717  7/1976  France .

*Primary Examiner*—Elizabeth McKane

[57] ABSTRACT

A device for using candle heat to diffuse aromatic oil, while avoiding overheating of the oil. A ring having an oil holding groove is supported by downwardly projecting tabs, from the candle holder, with the oil holding groove being above and encircling the candle flame, without any portion of the groove being directly over the flame. Radiant heat from the candle flame is conducted to the oil holding groove by means of radiation absorbing fingers projecting upward and inward from the ring. Several design features control the heat flow to the oil groove, including design choices of the width and number of the radiation absorbing fingers, and the number and angular size of a plurality of slots in the ring which block heat transfer at the locations of the slots, and the size of the outer diameter of the ring, from which some heat energy is radiated away from the device. The ring is constructed with compound bends for enhanced strength. The support tabs have sufficient depth to minimize spillage risk from tipping of the ring, by ensuring that the ring must be held level when inserting or removing it from the candle holder.

9 Claims, 2 Drawing Sheets

AROMA OIL CANDLE DIFFUSER RING

BACKGROUND OF THE INVENTION

The invention pertains to devices used for propagating aromatic oil through heating of the oil, and more specifically to such devices in which a candle flame is used as the source of heat.

As disclosed in applicant's information disclosure statement, there are a number of known devices, in which heat from candles, burners or light bulbs is used to disperse aromatic oils or other aromatic substances. In some prior devices, the aromatic substance is directly above the heat source, so that there is a risk of overheating of the aromatic oil or other aromatic substance. Overheating is undesirable, since, depending upon the particular aromatic oil or other substance used, overheating may present a fire hazard, and/or cause a change of chemical composition and aromatic properties of the oil, and/or cause excess diffusion of the oil, increasing oil consumption without providing additional benefits, where sufficient aroma is provided with less oil diffusion.

Applicant's invention, in the various forms claimed below, meets several needs not fully met by any prior device known to applicant, principally including: (1) the need to avoid overheating of the aromatic oil; (2) the associated need for design features which control the flow of heat to the aromatic oil; (3) the need to minimize the risks of spilling the aromatic oil and exposing the oil to the candle flame; (4) optimization of diffusion of the aromatic oil; and (5) prevention of overheating of the candle holder which could cause breakage of a glass candle holder and/or scorching of the surface on which the candle holder sits.

These and additional needs are met by applicant, through a device, supported from the candle holder, having a ring surrounding the candle flame, with a recessed groove as aromatic oil reservoir, with additional means for performing all needed functions, as described and claimed below.

SUMMARY OF THE INVENTION

The invention is a device for promoting diffusion of aromatic oil into room air, by heating the oil by heat from a candle flame of a candle housed in a candle holder, while avoiding overheating. The device comprises a ring having a recessed annular groove reservoir for holding the oil, the ring having securing means for securing the ring to the candle holder with the reservoir surrounding the candle flame without having any portion thereof directly above the candle flame; the ring also having radiant energy absorption means, for absorbing radiant energy from the candle flame and for conduction of heat energy to the reservoir for heating of the oil. The various forms of the invention also include various combinations of the following means: anti-tipping means, comprising part of the securing means, for so securing the ring to the candle holder in a manner so as to minimize the likelihood of spillage of oil by tipping of the ring; design means for controlling heat flow from the absorption means to the reservoir and to the candle holder; means for preventing ingress of oil toward the candle flame from overfilling of the reservoir; anti-wicking means for preventing wicking of the oil from the reservoir onto the surface of the ring; means for allowing adequate ventilation cooling of the candle holder; and means for enhancing structural strength of the ring. In the preferred embodiment: The securing means with anti-tipping means comprises three tabs projecting downward from the ring, which secure the ring to the interior of the candle holder, and have sufficient depth to insure that the ring must be moved only vertically when installing or removing it from the holder, so as to minimize the risk of oil spillage from tipping of the ring. The radiant energy absorption means comprises three raised fingers projecting upward and inward from the ring toward the flame, without covering the flame, which absorb and conduct radiant heat outward toward the reservoir. The design means for controlling heat flow to the oil reservoir and to the candle holder, comprises the width of the absorption fingers, as well as the number of said fingers, and both a plurality of slots in the ring, inward of the oil reservoir, which limit the portion of the ring through which radial outward heat flow may occur from the fingers toward the reservoir, and also the outer diameter of the ring, which conducts heat away to the air. The invention does not however include any means for allowing user adjustments during use of the ring. The means for preventing ingress of oil into the candle flame from any overfilling of the oil reservoir, is a lower height to the portion of the ring outside the reservoir, as compared to the interior portion, assuring that any oil overflow will move outward, away from the candle flame. The anti-wicking means comprises corners of at least about 90 degrees at the upper edges of the reservoir. The ventilation cooling means for cooling the candle holder, is a stepped segmented lower ring, which holds the rest of the ring above the candle holder and allows ventilation to flow through the gaps between the securing tabs. The strength enhancement means of the ring comprises compound bends in the reservoir and tab structure of the ring.

BRIEF DESCRIPTION OF THE DRAWINGS

Each of the drawings is a view of the same preferred embodiment.

DESCRIPTION OF THE PREFERRED EMBODIMENT

Figure 1:
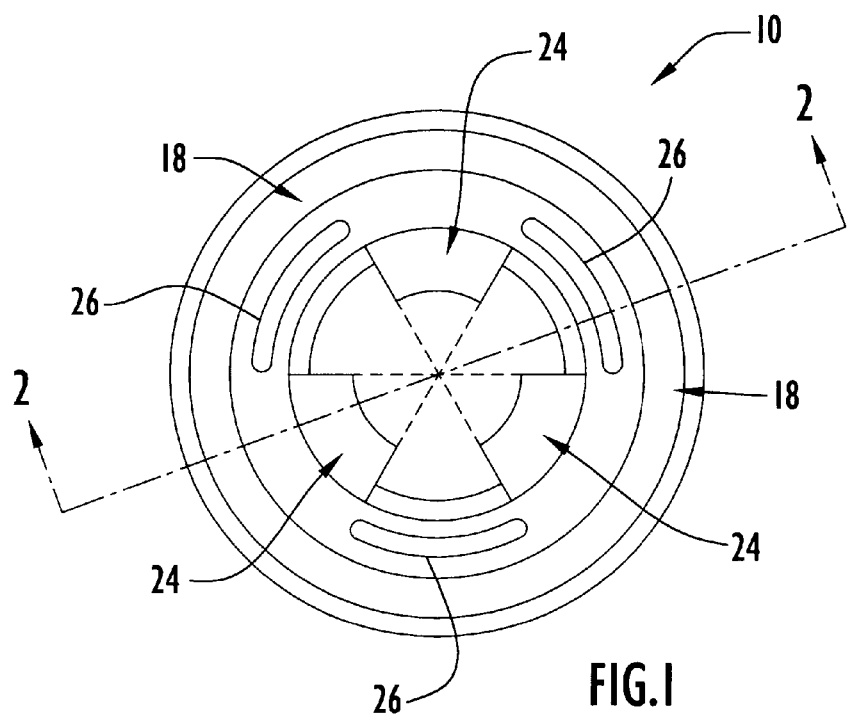
FIG. 1 is a plan view.

Referring now to the drawings, in which like reference numbers denote like or corresponding elements, the principal element of the device is an annular metal ring 10, further described in detail below, having an open central region to be positioned above the flame 12 of a candle 14 in the manner to be described; candle 14 rests in a candle holder 16. The embodiment shown is intended for use with a conventional candle holder 16 of the form of a shallow glass or cup having walls of form of a cylinder, open at the top and formed of glass, metal, or other non flammable material; however neither the candle holder 16 nor the candle 14 nor flame 12 are part of the invention, and are shown for explanatory purposes only.

The ring 10 has a recessed annular groove constituting an oil reservoir groove 18 for holding the aromatic oil to be heated and propagated into the air by the device. The oil reservoir groove 18 extends around the entire circumference of ring 10, in the preferred embodiment.

The securing means for securing the ring 10 to the candle holder 16 with the oil reservoir groove 18 surrounding the candle flame 12 without having any portion thereof directly above the flame 12, comprises three tabs 20, which project downward from the inner circular edge 22 of annular ring 10 and are equally spaced around the circumference of inner edge 22, which tabs 20 engage the inner walls of candle holder 16. With this structure, the annular ring 10 is oriented with the flame 12 beneath the open center of ring 10, so that oil reservoir groove 18 surrounds the flame 12 with no portion of oil reservoir groove 18 being directly above flame 12. The inner radius of ring 10 is selected such that the lower portions of tabs 20 will fit in a reasonably snug fit with the inner wall of candle holder 16, and the depth of the tabs 20 is sufficient, that the tabs 20 function as an anti-tipping means, for so securing the ring 10 to the candle holder 16 in a manner so as to minimize the likelihood of spillage of oil by tipping of the ring: The depth of the tabs 20 is sufficient to insure that the ring 10 can only be held in a substantially level orientation, when inserting or removing the device from the candle holder 16, so as to prevent spillage of aromatic oil from oil reservoir groove 18. For practical purposes the depth of tabs 20 must be at least about ten per cent of the diameter of inner edge 22 of ring 10.

The radiant energy absorption means, for absorbing radiant energy from the candle flame 12 and for conduction of heat energy to the oil reservoir groove 18, comprises the combination of the body of ring 10 and three metal fingers 24, spaced evenly around the circumference of inner edge 22 of ring 10, which fingers 24 project upward and inward from inner edge 22, and are thus positioned so as to absorb radiant energy from the flame 12, from which fingers 24 heat is conducted to oil reservoir groove 18 by fingers 24 and the body of ring 10. The fingers 24 do not project inward sufficiently so as to have any portion of any of the fingers 24 be directly above flame 12; this helps avoid excess heating of the aromatic oil in oil reservoir groove 18, although it is not critical in view of other heat flow control features discussed below.

The ring 10 contains three equally spaced slots 26, located between the angular positions of the fingers 24, which serve to impede heat flow to the oil reservoir groove 18 and to the candle holder 16, at least over the portions of the ring 10 where slots 26 are located, and also impede heat flow to oil reservoir groove 18 in those portions of ring 10, while not impeding outward heat flow from fingers 24 in the other portions of ring 10, between slots 26. The outward heat flow is also affected by the number and width of the fingers 24, as well as the outer diameter of ring 10, which effects radiation of heat from ring 10. A design means for controlling heat flow from the radiant energy absorption means to the oil reservoir groove 18 and to the candle holder 16 thus is afforded by selection of the combination of the number and width of the fingers 24, and the number, angular positions and angular widths of the slots 26, and the outer diameter of ring 10.

The means for preventing ingress of oil into the candle flame 12 from any overfilling of the oil reservoir groove 18, is afforded by the following structural feature of ring 10: The outer portion of ring 10, outside of oil reservoir groove 18, is at a lower height than the portion of ring 10 inside of oil reservoir groove 18, as shown in FIG. 2, so that, in the event of any overfilling of oil reservoir groove 18, the excess aromatic oil will flow outward, away from flame 12, rather than inward toward flame 12.

Figure 2:
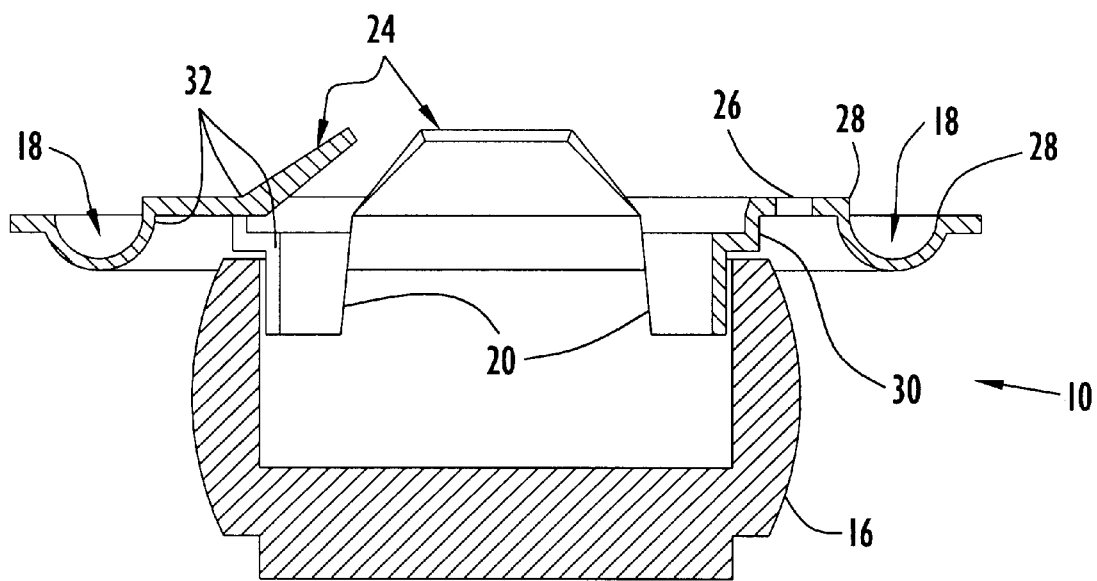
FIG. 2 is a sectional view as indicated by the section line 2—2 in FIG. 1, without the candle present.
Figure 3:
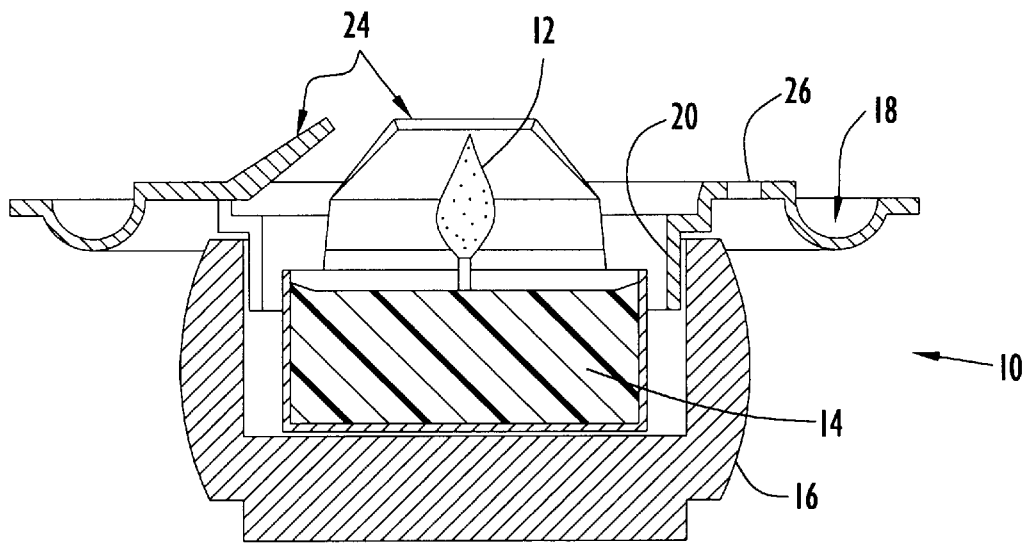
FIG. 3 is a reduced scale sectional view as in FIG. 2, but with the candle present.

The anti-wicking means for preventing wicking of the oil from the oil reservoir groove 18 onto the surface of the ring 10, is afforded by the sharp corners 28 at both of the upper edges of oil reservoir groove 18, as shown in FIG. 2. The corners 28 should have angles of at least about 90 degrees, or greater, to serve as effective anti-wicking means.

Figure 4:
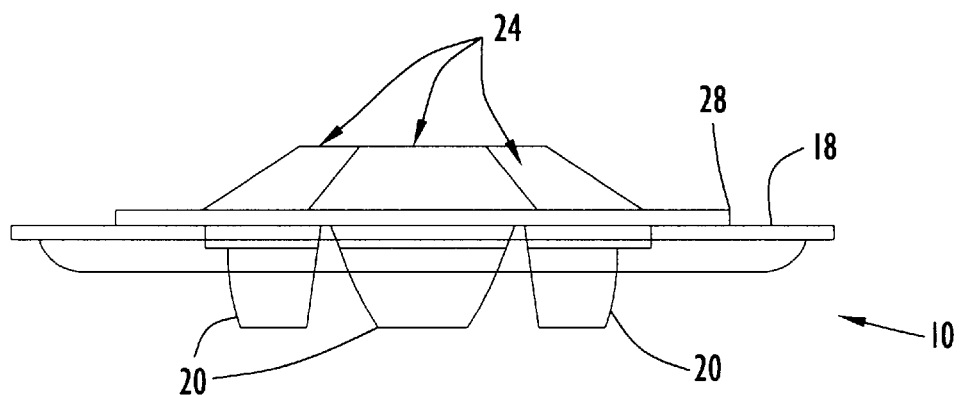
FIG. 4 is a side elevational view of the invention alone, without the candle holder or candle.

The means for allowing adequate ventilation cooling of the candle holder 16, is afforded by the following structural feature of the structure of ring 10: a stepped segmented lower ring 30, on the inside portion of ring 10, inside from the location of oil reservoir groove 18, which is lower than the main body of ring 10 and thus holds the main body of ring 10 up off of the top of candle holder 16, so as to prevent overheating of candle holder 16. The lower ring 30 is formed, in the one piece construction of the preferred embodiment, from the portion of the metal which further extends downward to form the tabs 20. The separation of the segments of lower ring 30 may be seen, albeit not very pronounced, in FIG. 4. Additional ventilation cooling for candle holder 16 is afforded by the fact that there are open spaces under the raised fingers 24.

The means for enhancing structural strength of the ring 10, is afforded by the use of compound bends 32 existing in ring 10 at the positions of oil reservoir groove 18, fingers 24, and tabs 20, in the preferred embodiment, in which ring 10 is fabricated from a single piece of 22 gauge sheet metal, 0.025" thick, which is suitably worked to form oil reservoir groove 18, fingers 24, and tabs 20. The term "compound bend" denotes a bend having more than one bend radius, which is stronger than a simple bend in resisting change of shape. Also, in the forming process, the metal is stretched and work hardened, using well known techniques, thus providing further bend resistance. It is desirable to fabricate the device with good structural strength, so that it may be used as a portable item, taken in the owner's luggage during travel, and thus may be subject to rough handling.

Those familiar with the art will appreciate that the invention may be employed in configurations other than the specific form disclosed above, without departing from the essential substance thereof.

For example, and not by way of limitation, although sheet metal steel is used to fabricate the preferred embodiment, the invention is not limited to the use of any particular material. Stainless steel, aluminum or copper could be used. The choice of materials is not necessarily limited to metals: one could instead possibly use glass, ceramic, or other nonflammable materials having sufficient heat conductivity, heat resistance and mechanical strength.

Similarly, although the preferred embodiment has a single circular oil reservoir groove 18, which extends around the entire angular circumference of ring 10, the invention is not necessarily limited to this form of oil reservoir groove 18. The oil reservoir groove 18 may instead be segmented, having multiple portions each extending over less than a complete circle. This would allow the use of different aromatic oils in different segments, for simultaneous vaporization of different aromatic oils. A single oil reservoir groove 18 may be used which does not form a complete circle, but has a gap, which gap may be used for grasping the ring 10 for insertion of tabs 20 into candle holder 16, or removal of tabs 20 from candle holder 16, when oil reservoir groove 18 is full of aromatic oil. Multiple oil reservoir grooves 18 may be used, with different radii. The use of multiple concentric oil reservoir grooves 18 would allow the device to heat oils in the various grooves to differing temperatures, which may be desirable for different aromatic oils having differing vaporization temperatures.

Although a circular ring 10, and a circular oil reservoir groove 18, are used in the preferred embodiment, it would not be necessary to use a precisely circular form; these members could be of elliptical form for example, although the use of an at least substantially circular form would be preferable for purposes of uniform heating of the aromatic oil. Accordingly the term "ring" is to be understood as not being necessarily limited to an object of precisely circular form.

Similarly the securing means of the preferred embodiment, for securing the ring 10 to the candle holder 16, may be varied in form as needed, to secure ring 10 to a candle holder 16 having a different geometry from the simple cylindrical cup geometry of the candle holder 16 with which the preferred embodiment is used. For a different candle holder geometry, it may be desirable or necessary to correspondingly vary the geometry of the tabs 20, and/or the shape of the inner edge 22 of ring 10, instead of using a circular shape for inner edge 22 as in the preferred embodiment.

Those familiar with the art will of course also appreciate that the invention is not limited to the use of any particular number of the tabs 20, or the radiation absorbing fingers 24, although three of each are used in the preferred embodiment. It is believed preferable to use at least three of each, though four or more could certainly be used instead. At least two of the tabs 20 are needed for secure positioning of the ring 10 with respect to the ring 10. At least two of the fingers 24 are needed to provide uniformity of heating of the aromatic oil, and use of more than two is better for uniform heating. It simplifies the geometry of the device to use equal numbers of the fingers 24 and the tabs 20.

The shape of the fingers 24 is not limited by functional considerations, since the radiation absorbing ability of each of the fingers 24 is determined instead by its area, particularly the area of the portion closest to the flame 12. The shapes of the fingers 24 may accordingly be varied as desired on the basis of aesthetic considerations.

And, although the device of the preferred embodiment is fabricated from a single piece of sheet metal, from which are formed not only the ring 10, but also the tabs 20 and fingers 24, it would of course be possible to fabricate these elements from separate pieces of metal, which could then be soldered, welded, or screwed together.

The scope of the invention is defined by the following claims, including also all subject matter encompassed by the doctrine of equivalents as applicable to the claims.

I claim:

1. A device for promoting diffusion of an aromatic oil into air by heating said oil by heat from a candle flame of a candle housed in a candle holder, said candle holder having interior walls, said device comprising:

(a) an annular ring, open in the middle of said ring;

(b) a reservoir for said oil, located upon said ring;

(c) securing means, attached to said ring, for securing said ring to the candle holder with said reservoir surrounding said candle flame without having any portion thereof directly above the candle flame;

(d) radiant energy absorption means, attached to said ring, for absorbing radiant energy from said candle flame and for conduction of heat energy to said reservoir for heating of said oil; and (e) ventilation cooling means allowing adequate space for ventilation cooling of the candle holder, wherein said ventilation cooling means comprises a stepped and segmented lower portion of said ring, interior from the portion of said ring containing said reservoir, wherein said stepped and segmented lower portion of said ring provides a separation between said radiant energy absorption means and the candle holder.

2. An aroma oil diffuser for heating aroma oil by application of heat from a candle flame, comprising:

an annular ring having an inner edge opposing an outer edge and top side opposing a bottom side, said annular ring including a recessed annular aroma oil reservoir groove defined between a substantially planar outer flange portion and a substantially planar inside portion, said groove having an outer circumferential edge proximate said outer flange portion and an inner circumferential edge proximate said inside portion;

wherein said substantially planar inside portion is disposed in a plane spaced above said outer flange portion;

wherein said groove inner circumferential edge is connected to said inside portion at a sharp corner, thereby providing an anti-wicking inner edge;

said ring including a radiant energy absorber projecting inwardly from said ring inner edge, wherein heat absorbed in said radiant energy absorber is thermally conducted to said groove via said ring inside portion;

said ring having a securing means supporting said ring such that said radiant energy absorber projects inwardly toward the candle flame and said recessed annular aroma oil reservoir groove surrounds the candle flame.

3. The aroma oil diffuser of claim 2, wherein said inside portion includes a plurality of slots.

4. The aroma oil diffuser of claim 2, wherein said sharp corner between said inside portion and said groove is a corner of 90 degrees.

5. The aroma oil diffuser of claim 2, wherein said annular ring is made of metal.

6. The aroma oil diffuser of claim 5, wherein said metal is aluminum.

7. The aroma oil diffuser of claim 5, wherein said metal is stainless steel.

8. The aroma oil diffuser of claim 5, wherein said metal is copper.

9. The aroma oil diffuser of claim 2, wherein said radiant energy absorber projecting inwardly from said ring inner edge comprises a plurality of metal fingers.

* * * * *